United States Patent [19]
Dewhurst et al.

[11] Patent Number: 5,541,338
[45] Date of Patent: Jul. 30, 1996

[54] FATTY IMIDAZOLINE CROSSLINKERS FOR POLYURETHANE, POLYURETHANEUREA AND POLYUREA APPLICATIONS

[75] Inventors: John E. Dewhurst, Macungie; James S. Emerick, Whitehall; Brian E. Farrell, Fogelsville, all of Pa.

[73] Assignee: Air Products and Chemicals, Inc., Allentown, Pa.

[21] Appl. No.: 408,456

[22] Filed: Mar. 22, 1995

[51] Int. Cl.$^6$ .................................................. C08G 18/65
[52] U.S. Cl. .................................. 548/313.7; 548/349.1; 528/73; 252/182.26
[58] Field of Search .................... 528/73; 252/182.26; 548/349.1, 313.7

[56] References Cited

U.S. PATENT DOCUMENTS

| | | | |
|---|---|---|---|
| 3,065,247 | 11/1962 | de Groote et al. | 260/404.5 |
| 4,374,222 | 2/1983 | Meyer | 524/241 |
| 4,433,067 | 2/1984 | Rice et al. | 521/51 |
| 4,444,910 | 4/1984 | Rice et al. | 521/51 |
| 4,546,114 | 10/1985 | Alberino et al. | 521/51 |
| 4,595,743 | 6/1986 | Laughner et al. | 528/73 |
| 4,696,771 | 9/1987 | Floyd | 260/404 |
| 4,764,540 | 8/1988 | Dewhurst et al. | 521/110 |
| 4,789,688 | 12/1988 | Dewhurst et al. | 521/110 |
| 4,886,838 | 12/1989 | Dewhurst | 521/117 |
| 4,897,428 | 1/1990 | Dewhurst et al. | 521/115 |
| 4,983,643 | 1/1991 | Sanna, Jr. | 521/159 |
| 5,019,600 | 5/1991 | Dewhurst | 521/117 |
| 5,076,989 | 12/1991 | Dewhurst | 264/300 |
| 5,155,182 | 10/1992 | Busba et al. | 525/526 |

*Primary Examiner*—Rachel Johnson
*Attorney, Agent, or Firm*—Michael Leach; William F. Marsh

[57] ABSTRACT

In an active hydrogen-containing B-side composition for reaction with a polyisocyanate-containing A-side composition to make a polyurethane, polyurethane/urea or polyurea elastomer by reaction injected molding, the improvement which comprises a crosslinking polyol composition which is the reaction product of a $C_{12}$–$C_{36}$ fatty acid with a polyalkylene polyamine to yield an intermediate imidazoline-containing polyamine reaction product having at least one $C_{11}$–$C_{35}$ alkyl substituent and further reacting the intermediate reaction product with a $C_2$–$C_{21}$ reactive epoxide.

17 Claims, No Drawings

FATTY IMIDAZOLINE CROSSLINKERS FOR POLYURETHANE, POLYURETHANEUREA AND POLYUREA APPLICATIONS

FIELD OF THE INVENTION

The present invention relates to crosslinker compositions for use in reaction injection molding of polyurethane, polyurethaneurea and polyurea articles.

BACKGROUND OF THE INVENTION

Reaction injection molding (RIM) is a versatile process by which elastomeric parts can be fabricated. The RIM process involves high pressure impingement mixing of a polyisocyanate stream (A-side) and an active hydrogen containing, isocyanate-reactive stream (B-side) followed by immediate injection into a closed mold. The primary appeal of this process lies in its inherently high productivity. One factor which limits productivity, however, is the ease of demolding the elastomeric parts. On the one hand, the system must cure fast enough for good green strength at demold while on the other it must not be so fast that large complicated molds cannot be filled. Ease of removal of the part from the mold is also important and is related to green strength as well as mold release agent used. Many internal mold release agents have been devised which provide ease of release at the expense of system reactivity, either making it more difficult to fill large molds or causing less than desirable green strength within acceptable demold times. In addition to system reactivity problems from internal release agents, inert inorganic fillers which are commonly used in elastomeric RIM systems for automotive applications can also cause brittleness or cheesiness at demold.

The B-side of elastomeric RIM systems is normally composed of a blend of a high molecular weight polyether polyahl for the soft block, a diol or diamine chain extender for the hard block and additives such as surfactants, flame retardants, catalysts and internal release agents. When the polyether is OH-terminated, such as a 6000 molecular weight triol, tin and tertiary amine catalysts are generally used.

In order to improve the properties of such RIM elastomers at demold, several approaches have been taken:

U.S. Pat. No. 4,433,067 discloses the use of polyether polyamines in place of the polyols, resulting in polyurea RIM systems which require no tin or amine catalysts.

U.S. Pat. No. 4,444,910 discloses the use of tin and amine catalysts in the aforementioned polyurea system for improved green strength.

U.S. Pat. No. 4,546,114 discloses the use of mold temperatures about 110° C. for improved green strength in polyurea systems.

U.S. Pat. No. 4,983,643 discloses the use of polyester-modified isocyanate prepolymers in the A-side of polyurea systems for reduced brittleness at demold.

U.S. Pat. No. 4,595,743 discloses the use of low molecular weight amine-initiated polyols as additives to these systems for higher crosslinking and improved green strength.

The use of low molecular weight, amine-initiated polyols is fairly well-known in the polyurethane industry for such applications as rigid foam. In addition, the use of fatty aminopolyols has been disclosed previously.

U.S. Pat. No. 4,696,771 discloses the synthesis of fatty amino polyols bearing a single tertiary amine group from the reaction of N-substituted ethanolamines with glycidyl ethers of fatty alcohols or glycidyl esters of fatty acids.

U.S. Pat. No. 4,897,428 discloses the use of specific fatty aminopolyols as compatibilizers for zinc laurate or zinc oleate in RIM as internal mold release agents.

U.S. Pat. Nos. 4,764,540 and 4,789,688 disclose the use of fatty aminopolyols bearing ether, ester and/or amide groups in RIM formulations for improved release.

U.S. Pat. No. 4,374,222 discloses the use of fatty amide-based polyols in polyurethanes as internal mold release agents.

U.S. Pat. No. 3,065,247 discloses the reaction of polyamines with equimolar amounts of epoxidized fatty acid esters of lower alcohols. An example would be butyl epoxystearate. These products are distinguished from those of the present invention in that: (1) they use equimolar amounts of reactants and therefore do not react all of the available NH groups; and (2) the fatty chains attached in the ring-opening reaction are attached at the middle instead of the ends. The products of U.S. Pat. No. '247 are described as useful as emulsifying agents in petroleum products and as corrosion inhibitors. Polyurethane applications are not mentioned.

U.S. Pat. Nos. 4,764,540; 4,789,688 and 4,847,307 disclose the use of imidazolines to neutralize highly acidic silicone internal mold release agents.

U.S. Pat. No. 5,076,989 discloses the use of imidazolines to compatibilize zinc stearate, laurate and oleate for purposes of internal mold release agents in RIM.

U.S. Pat. Nos. 4,886,838 and 5,019,600 discloses the use of salts of imidazolines with carboxylic acids to compatibilize zinc stearate, laurate and oleate as internal mold release agents in RIM.

SUMMARY OF THE INVENTION

The present invention is directed to crosslinking polyols which are useful in the manufacture of polyurethane, polyurethaneurea and polyurea elastomers. The present invention provides as the crosslinker a polyol of at least 3, preferably 3 to 6, primary and/or secondary hydroxyl groups and having at least one tertiary amino group and at least one imidazoline moiety containing an organic substituent of at least 10 carbon atoms. The polyol crosslinker is prepared by reacting a fatty acid with a polyalkylene polyamine to yield a fatty substituted imidazoline-containing polyamine and further reacting the imidazoline-containing polyamine with a reactive $C_2$–$C_{21}$ epoxide, preferably a glycidyl ether of a fatty alcohol or a glycidyl ester of a fatty acid. For purposes of this invention "fatty" means a $C_{12}$–$C_{36}$ organic radical.

Another embodiment of the invention is a polyol-containing B-side composition for reaction with a polyisocyanate-containing A-side composition for making a polyurethane, polyurethaneurea and/or polyurea elastomer. The B-side composition consists essentially of a polyol, urethane catalyst, the crosslinking polyol and optionally a diol and/or diamine chain extender and silicone surfactant.

Yet another embodiment of the present invention is a method for making a polyurethane, polyurethaneurea and/or polyurea elastomer in which a reactive mixture is formed in a mold cavity and cured. The reactive mixture contains a polyol, an organic polyisocyanate, a urethane catalyst, the above-described crosslinking polyol and optionally a diol and/or diamine chain extender and silicone surfactant.

Two structural features distinguish the crosslinkers of this invention. First is the presence of an imidazoline ring, in addition to a tertiary amine, in a polyol composition of hydroxy functionality greater than two. The imidazoline ring is highly basic, contributing catalytic activity much greater than simple tertiary amines.

Second is the presence of multiple fatty groups which, in the preferred embodiment, outnumber the active OH groups. This leads to low viscosity polyols which act as internal lubricants in polyurethane systems thereby enhancing release from the mold far better than conventional crosslinkers. The combination of high catalytic activity, crosslinking and internal lubrication make these materials unique as processability enhancers for RIM applications.

DETAILED DESCRIPTION OF THE INVENTION

The present invention is directed to a crosslinking polyol composition for use in a molding process, an isocyanate-reactive composition containing the crosslinker and the use of the crosslinker in a molding process.

The crosslinking polyol composition of the present invention comprises a polyol of at least 3, preferably 3 to 6, primary and/or secondary hydroxyl groups and having at least one tertiary amino group and at least one imidazoline moiety containing an organic substituent of at least 10 carbon atoms. The polyol composition preferably comprises the reaction product of a substantially stoichiometric mixture of a $C_{12}$–$C_{36}$ fatty acid and a polyalkylene polyamine of 3 to 6 amino groups to afford an imidazoline-containing polyamine having an organic substituent on the imidazoline moiety of 11 to 35 carbon atoms. This intermediate reaction product is then reacted with a $C_2$–$C_{21}$ reactive epoxide in a ratio of equivalents of epoxide to equivalents of active amino hydrogens ranging from 1:1 to 1:1.25.

The fatty acid may be a mono- or dicarboxylic acid having from about 12 to 36 carbon atoms such as, for example, lauric, myristic, linoleic, linolenic and montanic acids and preferably is tall oil fatty acid or a monocarboxylic acid with 16 to 18 carbon atoms such as palmitic acid, stearic acid or oleic acid.

Suitable polyalkylene polyamines for use in reacting with the fatty acid and preparing the imidazoline-containing intermediate reaction product include any linear or branched polyalkylene polyamine of at least 3 amino groups, preferably 4 to 5 amino groups, such as diethylenetriamine, dipropylenetriamine, triethylenetetramine, tripropylenetetramine, tetraethylenepentamine, tetrapropylenepentamine, pentaethylenehexamine and the like. The polyethylene polyamines are the preferred materials, especially tetraethylenepentamine.

Although any $C_2$–$C_{21}$ reactive epoxide can be used including mono- and diepoxides such as ethylene oxide, propylene oxide and butylene oxide, it is preferred to use the glycidyl esters of $C_{12}$–$C_{22}$ fatty acids, such lauric acid, oleic acid and stearic acid, monoglycidyl ethers of monoalcohols containing 8–18 carbon atoms, such as 2-ethyl-1-hexanol, dodecanol and oleyl alcohol, and epoxidized $C_{12}$–$C_{22}$ α-olefins, such as 1,2-epoxyhexadecane.

Illustrative of the crosslinker polyols of the invention is the preferred polyol which is the reaction product of tetraethylenepentamine with stearic acid yielding intermediate product (1), a polyamine bearing at least one fatty imidazoline moiety.

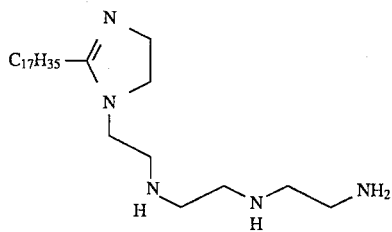

Polyamine (1) is reacted with the glycidyl ether of lauryl alcohol affording polyol (2) which contains more fatty chains than active OH groups.

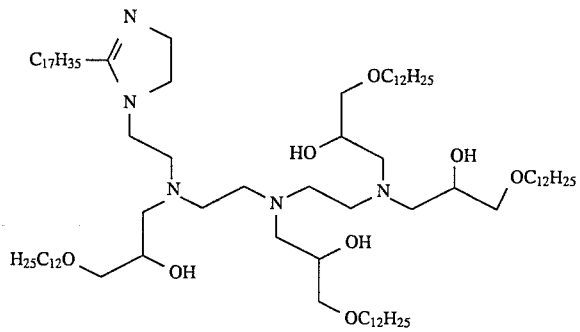

The crosslinking polyol compositions may generally be prepared by reacting a mixture of the polyamine and fatty acid together for a period of time at elevated temperatures and reduced pressure, for example, 225° C. and 55 mm Hg for four hours. Although the components may be reacted in various relative amounts, it is preferred to use substantially stoichiometric amounts of the acid and the polyamine. The resulting intermediate polyamine reaction product contains an imidazoline moiety to which is attached a substituent having at least 11 carbon atoms. This intermediate reaction product is next reacted with the reactive epoxide at >70° C. until the epoxide band at about 916 $cm^{-1}$ is absent from the infrared spectrum.

The crosslinking polyol compositions resulting from the reaction of the three components will have at least three, preferably 3 to 6, hydroxyl groups per molecule and at least one tertiary amine functionality and at least one imidazoline moiety containing an organo substituent of at least 11 carbon atoms, preferably a $C_{11}$–$C_{20}$ alkyl substituent. These polyol compositions are suitable for making either flexible or rigid, optionally cellular, polyurethane, polyurethane/urea or polyurea elastomers. The molded articles may possess various combinations of these properties such as rigid, non-cellular elastomers or flexible, cellular products for use, for example, as shoe soles.

The crosslinking polyol composition is used in an amount sufficient to neutralize acidic release agents which may be present; give good green strength due to catalysis and crosslinking; and/or enhance mold releasability. A suitable amount would be 0.5 to 10 wt%, preferably 3 to 5 wt%, based on the B-side, or isocyanate-reactive, composition comprising at least one high molecular weight active hydrogen containing compound (e.g., a polyol), amine and/or metallic urethane catalyst, optionally a diol or diamine chain extender, and silicone surfactant. The reaction mixture is preferably processed at an isocyanate index of from 70 to 130.

Suitable polyisocyanates for use in the present invention are aliphatic, cycloaliphatic, aralyphatic and aromatic polyisocyanates which are well known in the art. Specific examples include ethylene diisocyanate, 1,4-tetramethylene diisocyanate, 1,6-hexamethylene diisocyanate, cyclohexaneo-1,3- and 1,4-diisocyanates and isophorone diisocyanate. Typical aromatic polyisocyanates include phenylene diisocyanate, toluene diisocyanate and 4,4'-diphenylmethane diisocyanate. Especially suitable are the 2,4- and 2,6-toluene diisocyanates individually or together as their commercially available mixtures. Other especially suitable mixtures of diisocyanates are those known commercially as "crude MDI" also known as "PAPI", which contain about 60% of 4,4'-diphenylmethane diisocyanate along with other isomeric analogous higher polyisocyanates. Also suitable are prepolymers of these polyisocyanates comprising a partially prereacted mixture of polyisocyanate and polyether or polyester polyols disclosed hereinafter.

The polyether polyols useful in the invention include primary and secondary hydroxyl-terminated polyether polyols greater than 500 average molecular weight having from 2 to 6 functionality, preferably from 2 to 3, and a hydroxyl equivalent weight of from 250 to about 2500. Mixtures of polyether polyols may be used.

The polyether polyols are made from an appropriate initiator to which lower alkylene oxides such as ethylene oxide, propylene oxide, butylene oxide or mixtures thereof are added resulting in hydroxyl-terminated polyols. When two or more oxides are used, they may be present as random mixtures or as blocks of one or the other polyether. Thus the polyalkylene ether polyols include the poly(alkylene oxide) polymers, such as poly(ethylene oxide) and poly(propylene oxide) polymers and copolymers with a terminal hydroxyl group derived from polyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and like low molecular weight polyols.

In the practice of this invention, a single high molecular weight polyether polyol may be used. Also, mixtures of high molecular weight polyether polyols such as mixtures of di- and tri-functional materials and/or different molecular weight or different chemical composition materials may be used.

Useful polyester polyols include those produced by reacting a carboxylic acid with an excess of a diol; for example, adipic acid with ethylene glycol or butane diol, or a lactone with an excess of a diol, such as caprolactone and propylene glycol.

Illustrative of suitable hydroxyl group-containing chain extenders are ethylene glycol, propylene glycol, butane diols, 1,6-hexane diol, diethylene glycol, triethylene glycol, tetraethylene glycol, dipropylene glycol, tripropylene glycol, glycerol and trimethylol propane.

The aromatic diamine chain extenders useful in this invention include for example, 1-methyl-3,5-diethyl-2,4-diaminobenzene; 1-methyl-3,5-diethyl- 2,6-diaminobenzene (both these materials are also called diethyl toluenediamine or DETDA); 1,3,5-triethyl-2,6-diamino-benzene; 2,4-dimethyl-6-t-butyl-3,5-diaminobenzene; 3,5,3',5'-tetra-ethyl-4,4'-diaminodiphenylmethane; 1-methyl-3-t-butyl- 2,4-diaminobenzene; 1-methyl-5-t-butyl-2,6-diaminobenzene (both these materials are also called t-butyl toluenediamine or TBTDA) and the like. Particularly preferred aromatic diamine chain extenders are DETDA and TBTDA. It is within the scope of the invention to include some aliphatic chain extender materials as described in U.S. 4,246,363 and 4,269,945.

Urethane catalysts include amine and tin catalysts well known in the art such as for example, triethylenediamine and dibutyltin dilaurate. Suitable amounts of catalyst may range from about 0.025 to 0.3 parts, preferably 0.05 to 0.2 parts, per 100 parts per weight polyol in the elastomer composition.

Other conventional ingredients may be employed as needed, such as, for example, foam stabilizers, also known as silicone oils or surfactants and reinforcing materials.

The compositions according to the present invention may be molded using conventional processing techniques and are especially suited for processing by the RIM process. In general, two separate streams are intimately mixed and subsequently injected into a suitable mold, although it is possible to use more than two streams. The first stream contains the polyisocyanate component, while the second stream contains the polyol component, urethane catalyst, chain extender, the crosslinker polyol composition and any other additive which is to be included.

The following materials were used in the examples:

Multranol 9139—A glycerin-initiated polyoxyalkylene polyether triol having a hydroxyl number of 28—Miles, Inc.

Multranol 4050—An ethylenediamine-initiated polyoxyalkylene polyether tetrol with a hydroxyl number of 630—Miles, Inc.

Ethoduomeen T/13—A fatty amino triol from the ethoxylation of the reduction product of cyanoethylated tallow amine—Akzo Chemicals, Inc.

DETDA—80/20 mixture of 3,5-diethyl-2,4-toluenediamine and 3,5-diethyl-2,6-toluenediamine—Ethyl Corp.

XF-H1220—A neutral silicone internal mold release agent —Air Products and Chemicals, Inc.

Q2-7119—A carboxy-functional silicone internal mold release agent—Dow Corning.

DC 198—A silicone surfactant—Air Products and Chemicals, Inc.

DABCO® T-12—Dibutyltin dilaurate—Air Products and Chemicals, Inc.

DABCO T-1402—A hydroxy-functional organotin catalyst—Air Products and Chemicals, Inc.

DABCO 33LV®—A 33% solution of triethylenediamine in a glycol carrier—Air Products and Chemicals, Inc.

Mondur PF—4,4'-diphenylmethanediisocyanate which has been liquefied by reaction with a low mol wt glycol to an NCO content of about 22.6%—Miles, Inc.

Ancamid 506—an amido-amine curing agent having a very high imidazoline content from the reaction of tall oil with tetraethylene pentamine, having an amine NH eq wt of 105—Air Products and Chemicals, Inc.

Ancamid 503—An aliphatic amido-amine epoxy curing agent similar to Ancamid 506 but without the high imidazoline content and fatty groups.

Epodil 748—The glycidyl ether of lauryl alcohol—Air Products and Chemicals, Inc.

Epodil 746—The glycidyl ether of 2-ethyl-1-hexanol—Air Products and Chemicals, Inc.

EXAMPLE 1

370.0 grams of propylene oxide (6.37 eq) were added at a rate of 2 g/min to 668.37 grams of Ancamid 506 curing agent (6.37 eq) under nitrogen with stirring at 120° C. The reaction was held at 120° C. for 6 hours following the addition of the propylene oxide. The resulting product (Crosslinker 1) was an amber liquid.

EXAMPLE 2

A mixture of 600 grams of Epodil 748 epoxide (2 epoxy eq) and 210 grams of Ancamid 506 curing agent (2 NH eq) was stored at 70° C. overnight, after which the epoxide band at 912.7 cm$^{-1}$ was absent from the infrared spectrum. A low viscosity reddish liquid resulted (Crosslinker 2).

EXAMPLE 3

A blend of 300 grams of Epodil 746 epoxide (1.35 eq) and 300 grams of Ancamid 506 curing agent (3.86 eq) was kept at 70° C. overnight, after which the epoxide band at 912.7 cm$^{-1}$ was absent from the IR spectrum. This product (Crosslinker 3) was made with less epoxide so that some primary and secondary amino groups would be left.

EXAMPLE 4

A blend of 230 grams of Epodil 746 epoxide (1 eq) and 105 grams of Ancamid 506 curing agent (1 eq) were kept at 70° C overnight, after which the epoxide band at 911.9 cm$^{-1}$ was absent from the IR spectrum. This product is Crosslinker 4.

EXAMPLE 5

A blend of 240 grams of 1,2-epoxyhexadecane (1 eq) with 105 grams of Ancamid 506 curing agent (1 eq) was kept at 70° C. overnight, after which the epoxide band at 916.0 cm$^{-1}$ was absent from the IR spectrum. This product is Crosslinker 5.

EXAMPLE 6

A blend of 300 grams of Epodil 748 epoxide (1 eq) with 90 grams of Ancamid 503 curing agent (1 eq) was kept at 70° C. overnight, after which the epoxide band at 912.7 cm$^{-1}$ was absent from the IR spectrum. This Crosslinker 6 does not contain imidazoline rings.

EXAMPLES 7–13

The solubility of 2 parts of Q2-7119 acidic silicone release agent was tested in 5 parts of various crosslinkers, including Crosslinkers 2 and 4–6. The results are shown in Table 1.

TABLE 1

| Example | Combination | Result |
|---|---|---|
| 7 | Q2-7119 + Multranol 4050 | insoluble |
| 8 | Q2-7119 + Ethoduomeen T/13 | insoluble |
| 9 | Q2-7119 + Ancamid 506 | insoluble |
| 10 | Q2-7119 + Crosslinker 2 | soluble |
| 11 | Q2-7119 + Crosslinker 4 | insoluble |
| 12 | Q2-7119 + Crosslinker 5 | insoluble |
| 13 | Q2-7119 + Crosslinker 6 | insoluble |

The insolubility of this silicone makes it a powerful defoamer in polyol or polyamine blends. This silicone is usually not soluble in fatty solvents unless there is a chemical reaction such as neutralization of the acidic side chains. When the silicone dissolves in a neutralizing solvent there is an increase in viscosity because a salt is formed and the mixture is a single phase with no separation of layers upon standing. Examples 7, 8 and 13 show that without the imidazoline ring this neutralization does not take place and the silicone is insoluble. Upon standing overnight these samples separated into two liquid layers. Unexpectedly, only Crosslinker 2 with high imidazoline content and fatty alkoxide chains dissolved Q2-7119 (Example 10). Example 9 shows that the Ancamid 506 precursor to preferred Crosslinker 2 does not dissolve the silicone. Crosslinker 4 (Example 11) is insufficiently lipophilic and Crosslinker 5 (Example 12) does not contain the ether linkages which are apparently needed for this application.

REACTION INJECTION MOLDING (RIM) EXAMPLES

All RIM parts were made on a Battenfeld SHK 14 Piston Metering RIM Machine. Mold temperature was set at 60° C. and parts were demolded after one minute. An intricate mold was used incorporating a piston connected directly to a load cell to measure release force of the parts from the mold. The 7.95 mm diameter piston stuck into the bottom half, or cavity, of the mold, and the part was molded around the piston so that it was embedded into the part 9 mm deep. As the mold was opened at a slow, controlled rate the part was die-locked in the upper half of the mold by die-locking grooves and the force exerted by the part being pulled off of the piston was measured by the load cell. The data were transferred to an IBM PS/2 computer, where it was graphed. The spike showed the point of release and the ultimate force required. As parts were continuously shot into the mold without spraying, a graph of release force versus part number was made which allowed comparison of the releasability of various systems. A system which is not releasing well, such as one containing no internal mold release additives, will show a steady increase in force until 60 to 70 pounds are measured by the fifth shot. One which releases well shows a force plateau at forty pounds or lower out to ten to twenty shots.

EXAMPLES 14–16

These examples were run using oleic acid as the internal mold release agent with high levels of DABCO DC 198 silicone surfactant to aid release. Table 2 shows he RIM formulation components which are in parts by weight. The ratio of oleic acid molecules to imidazoline rings is constant in all three runs, as is the catalyst level, but only the fully alkoxylated Crosslinker 2 (Example 15) gave acceptable green strength. The release forces for Examples 14 and 15 are shown in Table 3.

TABLE 2

| Example | 14 | 15 | 16 |
|---|---|---|---|
| Multranol 9139 | 73.35 | 68.1 | 72.3 |
| DETDA | 16.5 | 18.0 | 18.0 |
| Multranol 4050 | 3.0 | | |
| Oleic Acid | 2.0 | 2.0 | 2.0 |
| Ancamid 506 | 2.25 | | |
| Crosslinker 2 | | 8.7 | |
| Crosslinker 3 | | | 4.5 |
| DABCO DC 198 | 2.7 | 3.0 | 3.0 |
| DABCO T-1402 | 0.2 | 0.2 | 0.2 |
| Mondur PF | 53.0 | 50.5 | 50.7 |
| Green Strength | Fair | Good | Poor |
| Release | Fair | Good | N.A. |

TABLE 3

| Part # | Example 14 - Ancamid 506 Force (pounds*) | Example 15 - Crosslinker 2 Force (pounds*) |
|---|---|---|
| 1 | 3.0 | 5.55 |
| 2 | 16.2 | 8.30 |
| 3 | 22.2 | 12.70 |
| 4 | 25.7 | 14.85 |
| 5 | 46.0 | 19.60 |
| 6 | 36.0 | 30.10 |

TABLE 3-continued

| Part # | Example 14 - Ancamid 506 Force (pounds*) | Example 15 - Crosslinker 2 Force (pounds*) |
|---|---|---|
| 7 | 51.0 | 34.65 |
| 8 | 43.0 | 45.00 |
| 9 | 58.0 | 45.00 |
| 10 | 65.0 | 39.00 |
| 11 |  | 40.00 |
| 12 |  | 41.00 |
| 13 |  | 42.00 |
| 14 |  | 43.00 |
| 15 |  | 43.00 |
| 16 |  | 37.00 |

*Pounds-force × 4.448 = Newtons

EXAMPLES 17–20

The polyurethane RIM formulations in Table 4 demonstrate the use of the new fatty imidazoline crosslinkers with zinc stearate as an internal mold release. The release forces (pounds-force) are shown in Table 5.

TABLE 4

| Example | 17 | 18 | 19 | 20 |
|---|---|---|---|---|
| Multranol 9139 | 79.5 | 70.1 | 77.5 | 77.5 |
| DETDA | 16.5 | 18.0 | 16.5 | 16.5 |
| Multranol 4050 | 3.0 |  | 3.0 |  |
| Crosslinker 2 |  | 8.7 |  | 3.0 |
| Zinc Stearate |  |  | 2.0 | 2.0 |
| DABCO DC 198 | 0.8 | 3.0 | 0.8 | 0.8 |
| DABCO T-12 | 0.1 |  | 0.1 | 0.1 |
| DABCO T-1402 |  | 0.2 |  |  |
| DABCO 33LV | 0.1 |  | 0.1 | 0.1 |
| Mondur PF | 50.0 | 50.7 | 50.0 | 50.0 |
| Green Strength | Good | Good | Good | Good |
| Release | Poor | Poor | Excellent | Excellent |

TABLE 5

| Part # | Example 7 Multranol 4050 | Example 18 Crosslinker 2 | Example 19 Multranol 4050 with Zn Stearate | Example 20 Crosslinker 2 with Zn Stearate |
|---|---|---|---|---|
| 1 | 8.14* | 27.8* | 4.91* | 6.30* |
| 2 | 19.54 | 26.1 | 5.80 | 8.60 |
| 3 | 31.06 | 31.5 | 6.71 | 9.90 |
| 4 | 43.20 | 38.0 | 7.64 | 12.60 |
| 5 | 52.60 | 48.0 | 8.97 | 13.10 |
| 6 | 59.80 | 53.0 | 10.37 | 18.60 |
| 7 | 66.10 | 56.0 | 11.10 | 24.90 |
| 8 |  | 61.0 | 11.43 | 21.90 |
| 9 |  | 72.0 | 13.10 | 27.50 |
| 10 |  | 73.0 | 10.07 | 21.10 |
| 11 |  |  | 11.60 | 21.70 |
| 12 |  |  | 11.67 | 22.00 |
| 13 |  |  | 10.77 | 20.50 |
| 14 |  |  | 12.97 | 20.10 |
| 15 |  |  | 15.57 | 20.20 |

*Pounds-force × 4.448 = Newtons

EXAMPLES 21–24

The following RIM systems in Table 6 were run to compare the effectiveness of the crosslinkers of this invention as processing aids in glass-filled elastomeric RIM using a silicone internal mold release (IMR). Example 24 shows that the fatty imidazoline crosslinker improves release and green strength at low catalyst levels. The release forces (pounds-force) are shown in Table 7.

TABLE 6

| Example: | 21 | 22 | 23 | 24 |
|---|---|---|---|---|
| Multranol 9139 | 79.5 | 76.3 | 74.3 | 69.0 |
| DETDA | 16.5 | 16.5 | 18.0 | 18.0 |
| Multranol 4050 | 3.0 | 3.0 |  |  |
| XF-H1220 |  | 4.0 | 4.0 | 4.0 |
| Crosslinker 1 |  |  | 3.5 |  |
| Crosslinker 2 |  |  |  | 8.9 |
| DABCO DC 198 | 0.8 |  |  |  |
| DABCO T-1 2 | 0.1 | 0.1 | 0.1 |  |
| DABCO T-1 402 |  |  |  | 0.1 |
| DABCO 33LV | 0.1 | 0.1 | 0.1 |  |
| Glass fibers | 26.5 | 26.5 | 26.6 | 26.5 |
| Mondur PF | 50.4 | 50.4 | 50.9 | 50.5 |
| Green Strength: | Good | Good | Excellent | Excellent |
| Release: | Poor | Fair | Fair | Good |

TABLE 7

| Part # | Example 21 No IMR | Example 22 Multranol 4050 | Example 23 Crosslinker 1 | Example 24 Crosslinker 2 |
|---|---|---|---|---|
| 1 | 17.4* | 9.7* | 11.5* | 7.6* |
| 2 | 68.0 | 17.8 | 25.0 | 20.9 |
| 3 | 60.5 | 23.4 | 28.3 | 20.0 |
| 4 | 68.5 | 26.6 | 27.3 | 21.3 |
| 5 |  | 32.8 | 29.4 | 23.6 |
| 6 |  | 34.0 | 34.8 | 19.7 |
| 7 |  | 42.0 | 43.0 | 27.4 |
| 8 |  | 46.0 | 51.0 | 29.3 |
| 9 |  | 50.0 | 52.0 | 33.5 |
| 10 |  | 52.0 | 61.0 | 41.0 |
| 11 |  |  |  | 23.0 |
| 12 |  |  |  | 29.2 |
| 13 |  |  |  | 42.0 |
| 14 |  |  |  | 47.0 |
| 15 |  |  |  | 43.0 |

Pounds-force × 4.448 = Newtons

The data in Table 6 shows that the two imidazoline crosslinkers provide better green strength than the Multranol 4050 crosslinker. The data in Table 7 shows that the imidazoline crosslinker from propylene oxide (Crosslinker 1 in Example 23) show no release advantage over Multranol 4050 crosslinker, whereas the imidazoline crosslinker with five fatty chains (Crosslinker 2 in Example 24) does.

EXAMPLES 25–27

These examples were run with oleic acid as the release agent. The ratio of oleic acid molecules to imidazoline rings (1:0.75) is constant throughout. Example 27 shows that the fugitive amine catalyst DABCO 33LV triethylenediamine can be eliminated from the blend .when using these crosslinkers. The release forces (pounds-force) are shown in Table 9.

TABLE 8

| Example | 25 | 26 | 27 |
|---|---|---|---|
| Multranol 9139 | 75.1 | 77.1 | 70.6 |
| DETDA | 16.5 | 18.0 | 18.0 |
| Multranol 4050 | 3.0 |  |  |
| Oleic Acid | 2.0 | 2.0 | 2.0 |
| Ancamid 506 | 2.25 |  |  |
| Crosslinker 1 |  | 3.6 |  |
| Crosslinker 2 |  |  | 8.7 |
| DABCO DC 198 | 0.8 | 0.5 | 0.5 |
| DABCO T-1402 | 0.25 | 0.2 | 0.2 |

TABLE 8-continued

| Example | 25 | 26 | 27 |
|---|---|---|---|
| DABCO 33LV | 0.1 | 0.1 | |
| Mondur PF | 50.0 | 48.0 | 50.5 |
| Green Strength | Good | Good | Excellent |
| Release | Good | Good | Good |

TABLE 9

| Part # | Example 25 Ancamid 506 | Example 26 Crosslinker 1 | Example 27 Crosslinker 2 |
|---|---|---|---|
| 1 | 5.05* | 5.00* | 5.40* |
| 2 | 11.95 | 16.60 | 9.20 |
| 3 | 20.50 | 28.80 | 21.70 |
| 4 | 22.95 | 40.00 | 31.00 |
| 5 | 24.85 | 23.00 | 34.00 |
| 6 | 33.35 | 23.40 | 31.70 |
| 7 | 28.80 | 26.40 | 32.80 |
| 8 | 32.00 | 30.30 | 37.30 |
| 9 | 31.10 | 33.30 | 41.00 |
| 10 | 30.95 | 37.30 | 44.00 |
| 11 | 37.60 | 36.10 | 41.90 |
| 12 | 42.85 | 29.90 | 38.40 |
| 13 | 38.90 | 30.40 | 45.00 |
| 14 | 32.60 | 30.20 | 44.70 |
| 15 | 32.60 | | 45.00 |

Pounds-force × 4.448 = Newtons

EXAMPLES 28 and 29

The RIM systems of Table 10 show the utility of the crosslinkers in a system using a combination of oleic acid and silicone internal mold release agents. Example 29 shows better release than Examples 27 and 28, even with a lower level of XF-H 1220. The release forces (pounds-force) are shown in Table 11.

TABLE 10

| Example: | 27 | 28 | 29 |
|---|---|---|---|
| Multranol 9139 | 70.6 | 76.3 | 68.1 |
| DETDA | 18.0 | 16.5 | 18.0 |
| Multranol 4050 | | | 3.0 |
| Oleic Acid | 2.0 | | 2.0 |
| Crosslinker 2 | 8.7 | | 8.7 |
| XF-H1220 | | 4.0 | 3.0 |
| DABCO DC 198 | 0.5 | | |
| DABCO T-12 | | 0.1 | |
| DABCO T-1402 | 0.2 | | 0.2 |
| DABCO 33LV | | 0.1 | |
| Mondur PF | 50.5 | 50.0 | 50.3 |
| Green Strength | Excellent | Excellent | Excellent |
| Release | Good | Good | Excellent |

TABLE 11

| Part # | Example 27 Crosslinker 2 with Oleic Acid | Exampkle 28 Multranol 4050 with Silicone | Example 29 Crosslinker 2 with Silicone and Oleic Acid |
|---|---|---|---|
| 1 | 5.40* | 8.75* | 3.90* |
| 2 | 9.20 | 17.50 | 5.15 |
| 3 | 21.70 | 18.60 | 6.70 |
| 4 | 31.00 | 20.05 | 3.50 |
| 5 | 34.00 | 22.70 | 9.90 |
| 6 | 31.70 | 22.30 | 9.30 |
| 7 | 32.80 | 28.90 | 13.35 |
| 8 | 37.30 | 27.55 | 22.75 |
| 9 | 41.00 | 28.65 | 25.95 |
| 10 | 44.00 | 29.35 | 27.40 |
| 11 | 42.90 | 29.40 | 31.20 |
| 12 | 38.40 | 26.95 | 32.25 |
| 13 | 45.00 | 26.30 | 33.45 |
| 14 | 44.00 | 30.15 | 33.60 |
| 15 | 44.70 | 28.70 | 31.70 |
| 16 | 45.00 | | 32.30 |
| 17 | | | 31.40 |

EXAMPLES 30–37

The RIM systems shown in Table 12 were part of a statistically designed experiment to optimize a RIM automotive fascia formulation. It can be seen that Example 33 using Crosslinker 2 gave the best balance of high flex and Young's modulus, high ultimate elongation and Die C tear strength and low heat sags (measured in millimeters).

TABLE 12

| Example | 30 | 31 | 32 | 33 | 34 | 35 | 36 | 37 |
|---|---|---|---|---|---|---|---|---|
| E-9139 | 74.3 | 72.6 | 77.9 | 69.2 | 76.3 | 70.6 | 79.9 | 67.2 |
| DETDA | 16.5 | 18.0 | 16.5 | 18.0 | 16.5 | 18.0 | 16.5 | 18.0 |
| M4050 | 3 | — | 3 | — | 3 | — | 3 | — |
| Crosslinker 2 | — | 8.7 | — | 8.7 | — | 8.7 | — | 8.7 |
| Zn St | 2 | — | 2 | — | — | 2 | 2 | — |
| XF-H1220 | 4 | — | — | 4 | 4 | — | — | 4 |
| DC 198 | — | 0.5 | 0.5 | — | — | 0.5 | 0.5 | — |
| DABCO T-12 | — | — | — | — | 0.1 | 0.1 | 0.1 | 0.1 |
| DABCO T-1402 | 0.1 | 0.1 | 0.1 | 0.1 | — | — | — | — |
| DABCO 33LV | 0.1 | 0.1 | — | — | 0.1 | — | 0.1 | — |
| Mondur PF | 49.9 | 50.7 | .50.2 | 50.4 | 50.1 | 50.5 | 50.4 | 50.2 |
| Flex Modulus | 33790 | 38223 | 37243 | 38957 1 | 33300 | 38737 | 22847 | 41770 |
| Young's Modulus | 25290 | 34474 | 21784 | 29110 1 | 22508 | 24822 | 18164 | 31620 |
| Elongation | 168 | 141 | 201 | 197 | 199 | 152 | 215 | 165 |
| Tear Strength | 478 | 565 | 493 | 568 | 631 | 545 | 584 | 478 |
| 4", 325° F. Sag | 37 | 31 | 120 | 27 | 28 | 48 | 39 | 48 |
| 6"250° F. Sag | 29 | 26 | 122 | 24 | 24 | 28 | 27 | 30 |

STATEMENT OF INDUSTRIAL APPLICATION

A crosslinking polyol composition is provided for making reaction injection molded polyurethane, polyurethane/urea and polyurea elastomeric articles.

We claim:

1. A polyol comprising at least three hydroxyl groups which are primary and/or secondary, at least one tertiary amino group and at least one imidazoline moiety containing an organo substiuent of at least 11 carbon atoms which is prepared by reacting a $C_{12}$–$C_{36}$ fatty acid with a polyethylene polyamine having at least four amino groups to yield an intermediate imidazoline-containing polyamine and further reacting the imidazoline-containing polyamine with a $C_2$–$C_{21}$ reactive monoepoxide.

2. The polyol of claim 1 in which the fatty acid is a tall oil fatty acid or a $C_{16}$–$C_{18}$ monocarboxylic acid.

3. The polyol of claim 1 in which the polyethylene polyamine is triethylenetetramine, tetraethylenepentamine or pentaethylenehexamine.

4. The polyol of claim 1 in which the reactive monoepoxide is a glycidyl ester of a $C_{12}$–$C_{22}$ fatty acid, a glycidyl ether of a monoalcohol containing 8–18 carbon atoms or an epoxidized $C_{12}$–$C_{22}$ α-olefin.

5. The polyol of claim 1 in which the fatty acid is stearic acid and the monoepoxide is glycidyl ether of lauryl alcohol.

6. The polyol of claim 4 which comprises the reaction product of a substantially stoichiometric mixture of the $C_{12}$–$C_{36}$ fatty acid and a polyethylene polyamine which is triethylenetetramine, tetraethylenepentamine or pentaethylenehexamine to afford an imidazoline-containing polyamine having an organic substituent on the imidazoline moiety of 11 to 35 carbon atoms which is then reacted with a $C_2$–$C_{21}$ reactive monoepoxide in a ratio of equivalents of epoxide to equivalents of active amino hydrogens ranging from 1:1 to 1:1.25.

7. The polyol of claim 6 in which the fatty acid is a tall oil fatty acid or a $C_{16}$–$C_{18}$ monocarboxylic acid.

8. The polyol of claim 6 in which the reactive monoepoxide is a glycidyl ester of a $C_{12}$–$C_{22}$ fatty acid, a glycidyl ether of a monoalcohol containing 8–18 carbon atoms or an epoxidized $C_{12}$–$C_{22}$ α-olefin.

9. The polyol of claim 6 in which the fatty acid is stearic acid and the monoepoxide is glycidyl ether of lauryl alcohol.

10. In an active hydrogen-containing B-side composition for reaction with a polyisocyanate-containing A-side composition to make a polyurethane, polyurethane/urea or polyurea elastomer by reaction injected molding, the improvement which comprises the B-side composition containing a crosslinking polyol which is prepared by reacting a $C_{12}$–$C_{36}$ fatty acid with a polyethylene polyamine which is triethylenetetramine, tetraethylenepentamine or pentaethylenehexamine to yield an intermediate imidazoline-containing polyamine and further reacting the imidazoline-containing polyamine with a $C_2$–$C_{21}$ reactive monoepoxide.

11. The B-side composition of claim 10 in which the fatty acid is a tall oil fatty acid or a $C_{16}$–$C_{18}$ monocarboxylic acid.

12. The B-side composition of claim 10 in which the reactive monoepoxide is a glycidyl ester of a $C_{12}$–$C_{22}$ fatty acid, a glycidyl ether of a monoalcohol containing 8–18 carbon atoms or an epoxidized $C_{12}$–$C_{22}$ α-olefin.

13. The B-side composition of claim 10 which comprises the reaction product of a substantially stoichiometric mixture of the $C_{12}$–$C_{36}$ fatty acid and the polyethylene polyamine to afford an imidazoline-containing polyamine having an organic substituent on the imidazoline moiety of 11 to 35 carbon atoms which is then reacted with a $C_2$–$C_{21}$ reactive monoepoxide in a ratio of equivalents of epoxide to equivalents of active amino hydrogens ranging from 1:1 to 1:1.25.

14. The B-side composition of claim 13 in which the fatty acid is a tall oil fatty acid or a $C_{16}$–$C_{18}$ monocarboxylic acid.

15. The B-side composition of claim 14 in which the reactive monoepoxide is a glycidyl ester of a $C_{12}$–$C_{22}$ fatty acid, a glycidyl ether of a monoalcohol containing 8–18 carbon atoms or an epoxidized $C_{12}$–$C_{22}$ α-olefin.

16. The B-side composition of claim 13, in which the fatty acid is stearic acid and the monoepoxide is glycidyl ether of lauryl alcohol.

17. In an active hydrogen-containing B-side composition for reaction with a polyisocyanate-containing A-side composition to make a polyurethane, polyurethane/urea or polyurea elastomer by reaction injected molding, the improvement which comprises the B-side composition containing a crosslinking polyol comprising at least three hydroxyl groups which are primary and/or secondary, at least one tertiary amino group and at least one imidazoline moiety containing an organo substiuent of at least 11 carbon atoms.

* * * * *